US011433249B1

(12) United States Patent
Shaker et al.

(10) Patent No.: US 11,433,249 B1
(45) Date of Patent: Sep. 6, 2022

(54) COMPACT AED WITH ONE DISTAL ELECTRODE

(71) Applicant: ALTRIX MEDICAL, INC., Centreville, VA (US)

(72) Inventors: Matthew Robert Shaker, Centreville, VA (US); Daniel Fleck, Potomac, MD (US); Andrew Reed, Trumbull, CT (US); Trent Quick, Polk City, IA (US); David Mathieu, Ocala, FL (US)

(73) Assignee: ALTRIX MEDICAL, INC., Centreville, VA (US)

( * ) Notice: Subject to any disclaimer, the term of this patent is extended or adjusted under 35 U.S.C. 154(b) by 0 days.

(21) Appl. No.: 17/712,881

(22) Filed: Apr. 4, 2022

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/0492* (2013.01)

(58) Field of Classification Search
CPC ..... A61N 1/3904; A61N 1/046; A61N 1/0492
See application file for complete search history.

(56) References Cited

U.S. PATENT DOCUMENTS

| | | | |
|---|---|---|---|
| 6,477,430 B1 | 11/2002 | Feuersanger et al. | |
| 8,489,207 B1 | 7/2013 | Vaisnys et al. | |
| 10,799,709 B2* | 10/2020 | Teber | A61N 1/046 |
| 10,953,234 B2* | 3/2021 | Kumar | A61B 5/341 |
| 11,103,718 B2 | 8/2021 | Montague et al. | |
| 11,185,709 B2* | 11/2021 | Kumar | A61N 1/3987 |
| D942,013 S | 1/2022 | Heusdens | |
| 11,253,715 B2* | 2/2022 | Kumar | A61B 5/282 |
| 2002/0156506 A1* | 10/2002 | Kroll | H01M 50/247 607/5 |
| 2004/0260376 A1* | 12/2004 | Craige | A61N 1/046 600/382 |
| 2008/0033495 A1* | 2/2008 | Kumar | A61N 1/3968 607/5 |
| 2011/0077497 A1* | 3/2011 | Oster | A61B 5/259 600/300 |
| 2014/0317914 A1* | 10/2014 | Shaker | A61N 1/046 29/825 |
| 2017/0056682 A1* | 3/2017 | Kumar | A61N 1/046 |
| 2019/0022400 A1* | 1/2019 | Kumar | A61B 5/361 |
| 2020/0222707 A1* | 7/2020 | Kumar | G16H 20/30 |
| 2020/0282225 A1* | 9/2020 | Kumar | A61N 1/046 |
| 2021/0213296 A1* | 7/2021 | Kumar | A61B 5/4818 |
| 2022/0134121 A1* | 5/2022 | Kumar | A61N 1/046 607/7 |

* cited by examiner

*Primary Examiner* — Eric D. Bertram
(74) *Attorney, Agent, or Firm* — Louis Ventre, Jr.

(57) ABSTRACT

A re-usable, compact automated external defibrillator (AED) having a proximate electrode and a distal electrode for use in delivering an electrical charge to a person in cardiac distress. The components of the AED are packed together in a low-profile device body. The distal electrode may be easily unpacked from the device body and deployed. A circuit board within the device body controls the AED. The proximate electrode is part of the device body such that the device body is attached to the skin of the person when in use. The distal electrode is wired to the device body and also attached to the skin of the person when in use. The circuit board may be used to deliver a biphasic electrical charge to the person. The adhesive pads on the electrodes may be peeled off and replaced for reuse. Also, the electrodes may be replaced, if needed.

11 Claims, 10 Drawing Sheets

COMPACT AED WITH ONE DISTAL ELECTRODE

TECHNICAL FIELD

In the field of light, thermal, and electrical application, a device for applying electrical energy to the external surface and inside portions of the body to restore normal operation of the heart.

BACKGROUND ART

The International Electrotechnical Commission (IEC) is a worldwide organization for standardization comprising all national electrotechnical committees (IEC National Committees). The object of IEC is to promote international co-operation on questions concerning standardization in the electrical and electronic fields. The IEC publishes a standard for Medical electrical equipment at Part 2-4: Particular requirements for the basic safety and essential performance of cardiac defibrillators IEC 60601-2-4, which discusses requirements for the basic safety and essential performance of cardiac defibrillators. Among other things, it specifies requirements for the defibrillator electrodes. This governing standard is used to develop and package pads for defibrillators.

The compact automated external defibrillator disclosed herein is a unique and improved way to implement and package electrodes that are compliant with this standard (with the possible exception of cord length, which may be less than the standard but such new length is justified by the fact that the improvements discussed herein enable the automated external defibrillator (AED) pads to be in closer proximity to the device body when used as compared to other AEDs).

An AED uses two electrodes, each with a conductive gel to help transfer an AED shock to a patient. The standard calls for the minimum active gel area of self-adhesive electrodes to measure a total of 150 square centimeters, with each area being at least 50 square centimeters for adults. Pediatric pads are required to total 45 square centimeters, with each area being at least 15 square centimeters (when pediatric electrodes are used).

Most AEDs today have electrodes that are the same size and package these pads either in the AED or the AED carrying case. The electrodes are typically in a pouch but there are other packaging methods. When the AED is used, the pouch is removed from the AED or AED case and opened. A protective layer is peeled from the electrode, revealing an adhesive layer. The adhesive is conductive and typically a hydrogel formula. The electrodes are adhered to the patient in specified locations. Because there are two electrodes, there are typically two cords (this is not the case in the present compact automated external defibrillator).

SUMMARY OF INVENTION

A re-usable, compact automated external defibrillator (AED) having a proximate electrode and a distal electrode for use in delivering an electrical charge to a person in cardiac distress. The components of the AED are packed together in a low-profile device body. The distal electrode may be easily unpacked from the device body and deployed. A circuit board within the device body controls the AED. The proximate electrode is part of the device body, which is attached to the skin of the person when in use.

The distal electrode is wired to the device body and also attached to the skin of the person with an adhesive when in use, which may be thought of as an adhesive pad. The circuit board may be used to deliver a biphasic electrical charge to the person. The distal electrode has a backing, typically made of foam, which may be thought of as a foam pad. The distal pad and electrode assembly is designed to be replaced if needed, for example after it has been used.

Stranded wire may be used to connect the distal electrode to the device body in order to maintain a compact AED profile. One or more liners may be used to separate the sticky parts of the pads from each other when stored in compacted form within the device body. To enable testing of the components prior to use, the liner separating the pads of the electrodes may define a hole through which an electrical connection is made between the proximate electrode and the distal electrode. This hole enables electrical contact when running a check on the operability of a discharge circuit. A metalized surface on the device body and the rear cover enable sealing the device body to preclude air infiltration that can dry out the pads. In another embodiment, a packaging envelope may separate the hydrogel and the proximate electrode. The packaging envelope is used to seal the AED adhesive pads to keep them from drying out when in storage and may include a pull-tab to unseal the pads and connect the proximate pad to the proximate electrode during a rescue.

Technical Problem

AED's are often too large for convenient transport and use. Adding to this problem is cord storage. According to the IEC 60601-2-4 standard, each cord leading from the AED device and ending at a pad should be least 1 meter. Most AEDs today have two pads that are the same size, which are typically packaged with the AED or are in an AED carrying case. Also, typical pads are packaged within a sealed pouch or tray. When the AED is needed for use, the pouch or tray is opened and the pads within are connected to the AED (if not pre-connected) and then attached to the patient.

The typical pads are composed of a foam backing and an electrode that have a protective layer or liner that is peeled from the pad, revealing an adhesive layer for placement on the patient. The pad is usually coated with hydrogel, which is electrically conductive. The pads are adhered to the patient in requisite locations with the hydrogel or other adhesive gel on the patient's skin. Because there are two pads, there are typically two cords that are unwound to extend between the charging unit and the pads in position on the patient. Pads are often connected to the AED through a plug.

A challenge to storing pads for most AEDs involves the conductive material on the metal surface, typically a hydrogel formula. These formulas typically require special storage to minimize exposure to air in order to keep the hydrogel from drying out (i.e. reduce evaporative drying), thereby extending the shelf life of the electrode pads.

Solution to Problem

The solution is a compact AED that employs a single cord when in use to minimize AED weight, volume and deployment operations. The single cord joins a remote pad with the AED, where the AED itself doubles function to serve as one of the pads.

The compact automated external defibrillator minimizes space required to store the pads with the AED by using an alternative configuration.

The solution seals the compact automated external defibrillator from air infiltration to protect the pads from drying out.

The solution of adhering the AED device to the patient is desirable because the compact automated external defibrillator is small and attaching it ensures that the AED is stable and does not "fly around" during the rescue event. Adhering the AED device to the patient limits possible injuries to the patient or bystanders and also provides added confidence that the electrical connections are maintained.

Advantageous Effects of Invention

The solution disclosed herein minimizes the physical volume required to store the pads with the AED.

The solution disclosed herein employs an alternative configuration for the AED where the AED attaches to the patient, requiring only one remote pad for operability.

The preferred solution disclosed herein strives to minimize duplication of component parts within the AED to provide an AED operable with fewer component parts than AEDs heretofore available.

The solution disclosed herein provides a reusable AED once the pads are replaced, which reduces replacement costs and adds to functionality.

The solution disclosed herein extends the life of the AED by allowing hydrogel, or other adhesive, to be replaced prior to or after expiration.

This solution enables the use of pads having different sizes, and complies with IEC60601-2-4 requirements for total area and minimum individual area.

This solution still utilizes two electrodes, one electrode is connected directly (no wire) with hydrogel or a similar adhesive to both the patient and the energy source within the AED while the other is connected to the energy source by a wire and adhered to the patient.

BRIEF DESCRIPTION OF DRAWINGS

The drawings illustrate preferred embodiments of the Compact AED with One Distal Electrode according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate several embodiments of the compact automated external defibrillator (100) as disclosed herein. The drawings and the preferred embodiments of the compact automated external defibrillator (100) are presented with the understanding that the compact automated external defibrillator (100) is susceptible of embodiments in many different forms and, therefore, other embodiments may be utilized and structural, and operational changes may be made, without departing from the scope of the present invention.

Figure 1:
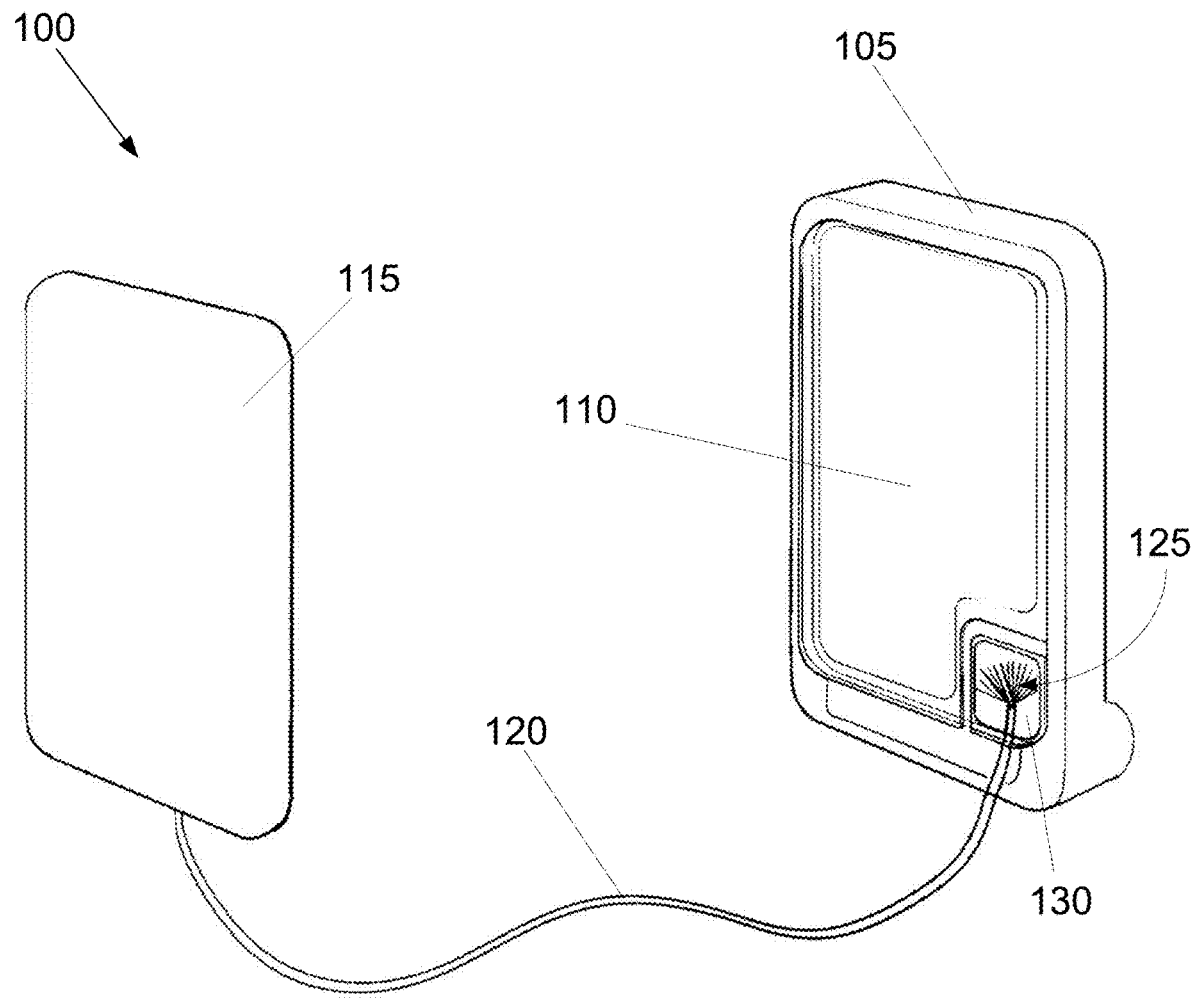
FIG. 1 is a perspective of the distal electrode separated from the device body.
Figure 4:
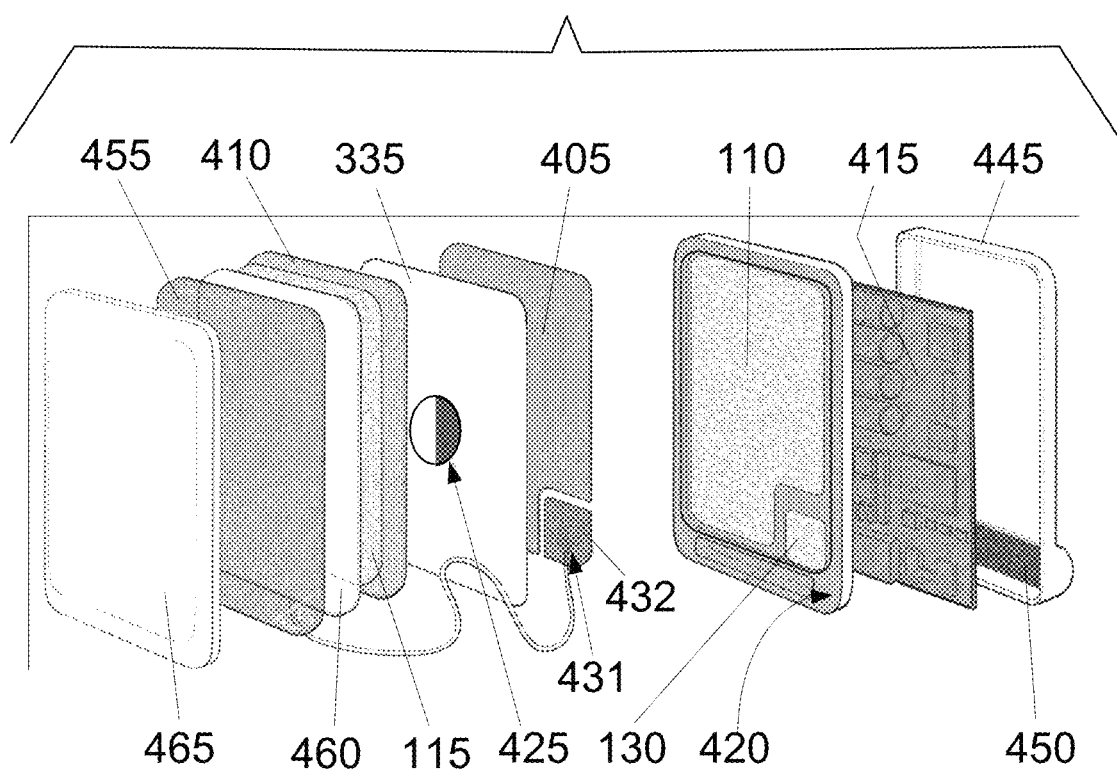
FIG. 4 is an exploded view of the compact AED with one distal electrode.
Figure 5:
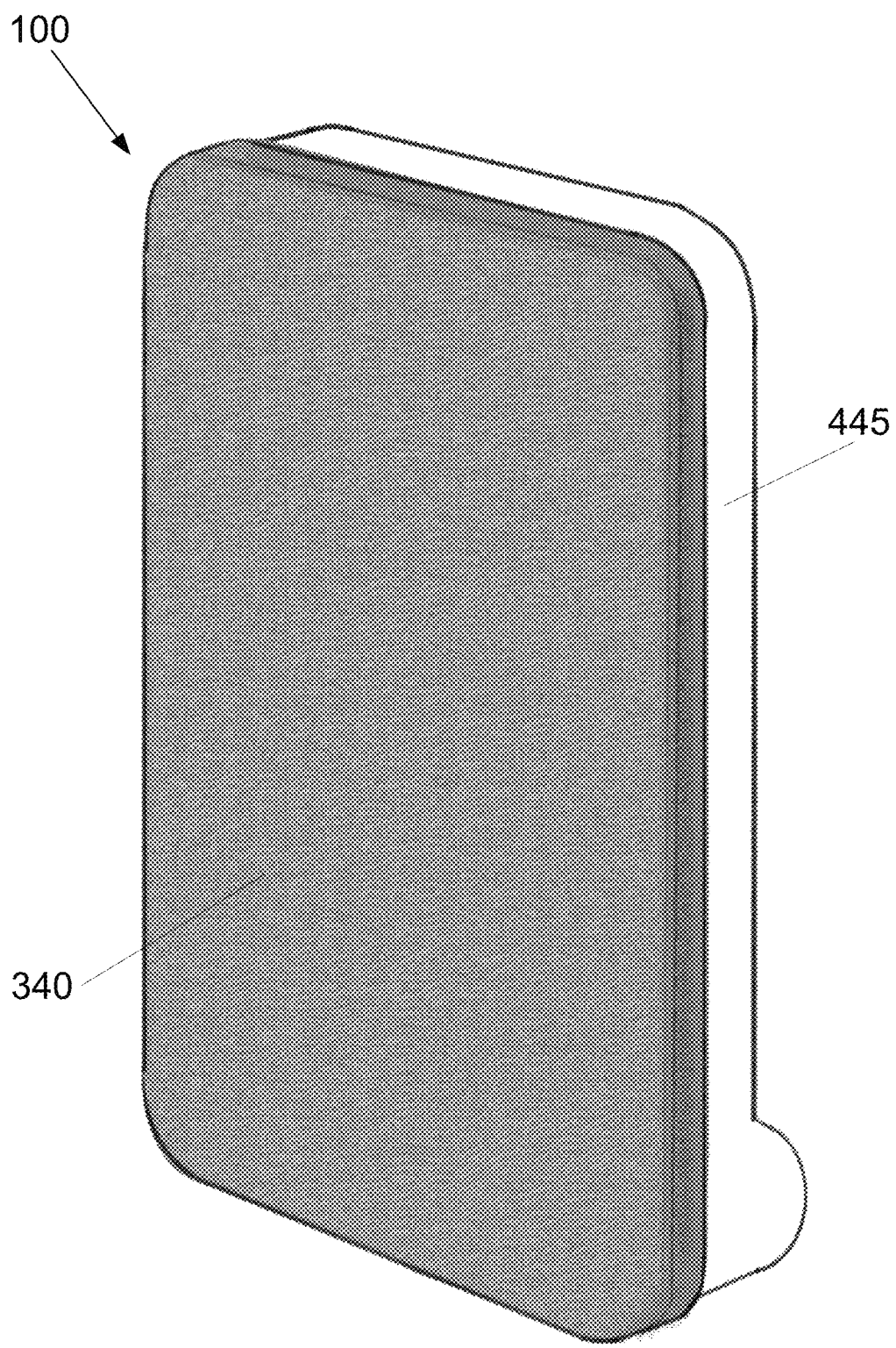
FIG. 5 is a perspective view of the rear of the compact AED with one distal electrode.
Figure 6:
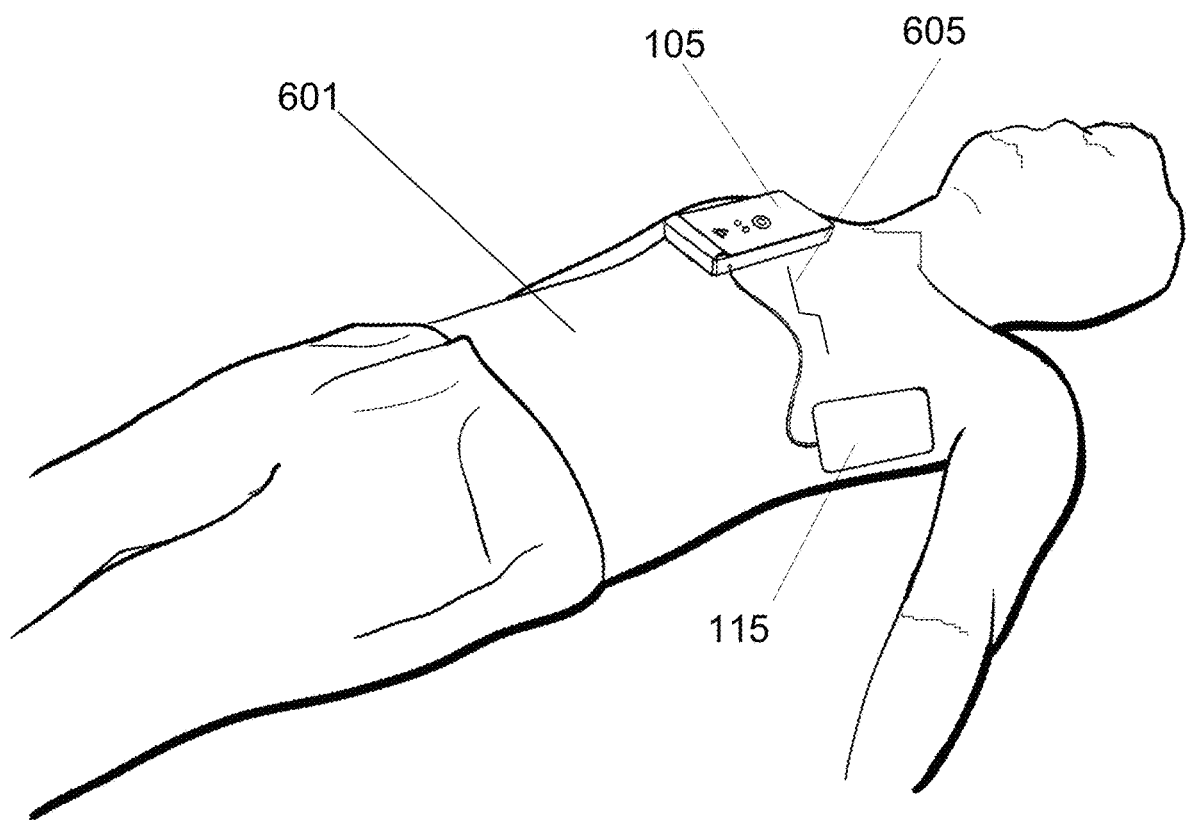
FIG. 6 is a perspective view of a person in cardiac distress with the compact AED with one distal electrode attached to the person.

FIG. 1 is a front perspective view of the compact automated external defibrillator (100) with a distal electrode (115) shown separated from its storage position in the device body (105). The compact automated external defibrillator (100) may be referred to herein as the AED. FIG. 4 shows an exploded view of important components of the compact automated external defibrillator (100).

The compact automated external defibrillator (100) is configured to deliver an electrical charge (605) to a person (601) in cardiac distress. The compact automated external defibrillator (100) is further configured to support a plurality of cardiac rescues because it is reusable on another person (601), preferably after the foam pad (460), distal electrode (115), and distal pad (410) are removed and replaced, and also after the proximate pad (405) and the liner (335) have been removed and replaced.

The compact automated external defibrillator (100) includes a device body (105) that houses the components of the compact automated external defibrillator (100), which may be referred to herein as the AED. The AED operationally functions using a circuit board (415) within the device body (105) that permits a battery (450) also within the device body (105) to energize both electrodes. The battery (450) is preferably lodged at the base of the device body (105) on its front side, which is shown in FIG. 4 on the right of the exploded view and within a front body housing (445). Preferably, the battery (450) is not part of, or mounted to, the circuit board. The rear cover (465) is shown to the left-side of the exploded view of the device body (105) in FIG. 4.

The device body (105) contains a proximate electrode (110) and a distal electrode (115). The proximate electrode (110) is an integrated part of the device body (105). It is preferably supplemented by a proximate pad (405), which is preferably made of an electrically conducting adhesive gel, such as hydrogel. If hydrogel is not used, the proximate pad (405) may include a skin adhesive (905) that is made to stick to the skin of a person (601) in cardiac distress. An electrode adhesive (910) may be applied to adhere the proximate pad (405) to the proximate electrode (110).

The proximate pad (405) is electrically conductive and is thus able to conduct the electrical charge (605) to or from the proximate electrode (110).

The proximate pad (405) is preferably the larger of the two pads. The proximate pad (405) is connected to the AED by adhering or fastening to the device body (105). The proximate pad (405) and the distal pad (410) are preferably made of hydrogel. The term "pad" is used loosely in this sense that the proximate pad (405) and the distal pad (410) may be formed simply by applying hydrogel adhesive in lines, dashed lines, or lots of tiny dots. In practice, the substance forming the proximate pad (405) and the distal pad (410) may not be considered by some to be a pad in the traditional sense of it being a thick piece of soft material. Hydrogel or another adhesive may be similarly applied to the connecting electrode (130) and insulating cover (432). The connecting electrode (130) is preferably tin or silver.

Thus, the device body (105) is configured to operably integrate with the proximate electrode (110). To facilitate reuse of the AED with new adhesive pads, the proximate pad (405) is a removable part of the proximate electrode (110) and also a removable part of the device body (105). The proximate electrode (110) is restored to near-new condition by peeling off the used proximate pad (405) and adhering a new replacement pad to the proximate electrode (110). The proximate pad (405), liner (335), distal pad (410), distal electrode (115), foam pad (460), and packing cover (455) may also be removed and replaced should that become necessary for any reason.

The distal electrode (115) is configured to be easily unpacked from the device body (105) to deploy on the person (601) in cardiac distress. Preferably, a liner (335) is placed between the two electrodes so that the distal electrode (115) can be easily separated from the proximate electrode (110) and unpacked from the device body (105). More precisely, in a preferred embodiment, the liner (335) is placed between the proximate pad (405) and the distal pad (410) to keep them from sticking together when separated during an emergency. The liner (335), the proximate pad (405), distal electrode (115), distal pad (410), foam pad (460), packing cover (455), wire (120), and insulating cover (432) are user replaceable. In another embodiment, a second liner is provided on the other side of the proximate pad (405) prior to installation onto the proximate electrode (110) to aid in shipping and packaging the proximate pad (405). This second liner faces the proximate electrode (110) and is removed from the proximate pad (405) prior to installation on the proximate electrode (110).

In an alternative embodiment, the distal electrode (115), the proximate electrode (110), or the connecting electrode (130) can made of a carbon-loaded vinyl, which is an electrically conductive material and can serve as a substitute for tin or silver.

In another alternative embodiment, the distal electrode (115) is twice the size of the pad geometry and then folded over on itself with the splayed wire strands between the layers of distal electrode (115). A layer of electrode adhesive (910) holds together the strands (125) of the wire (120) and the folded distal electrode (115). The benefit of this embodiment is that it provides a higher level of surface area between the distal electrode (115) and the strands (125).

Figure 2:
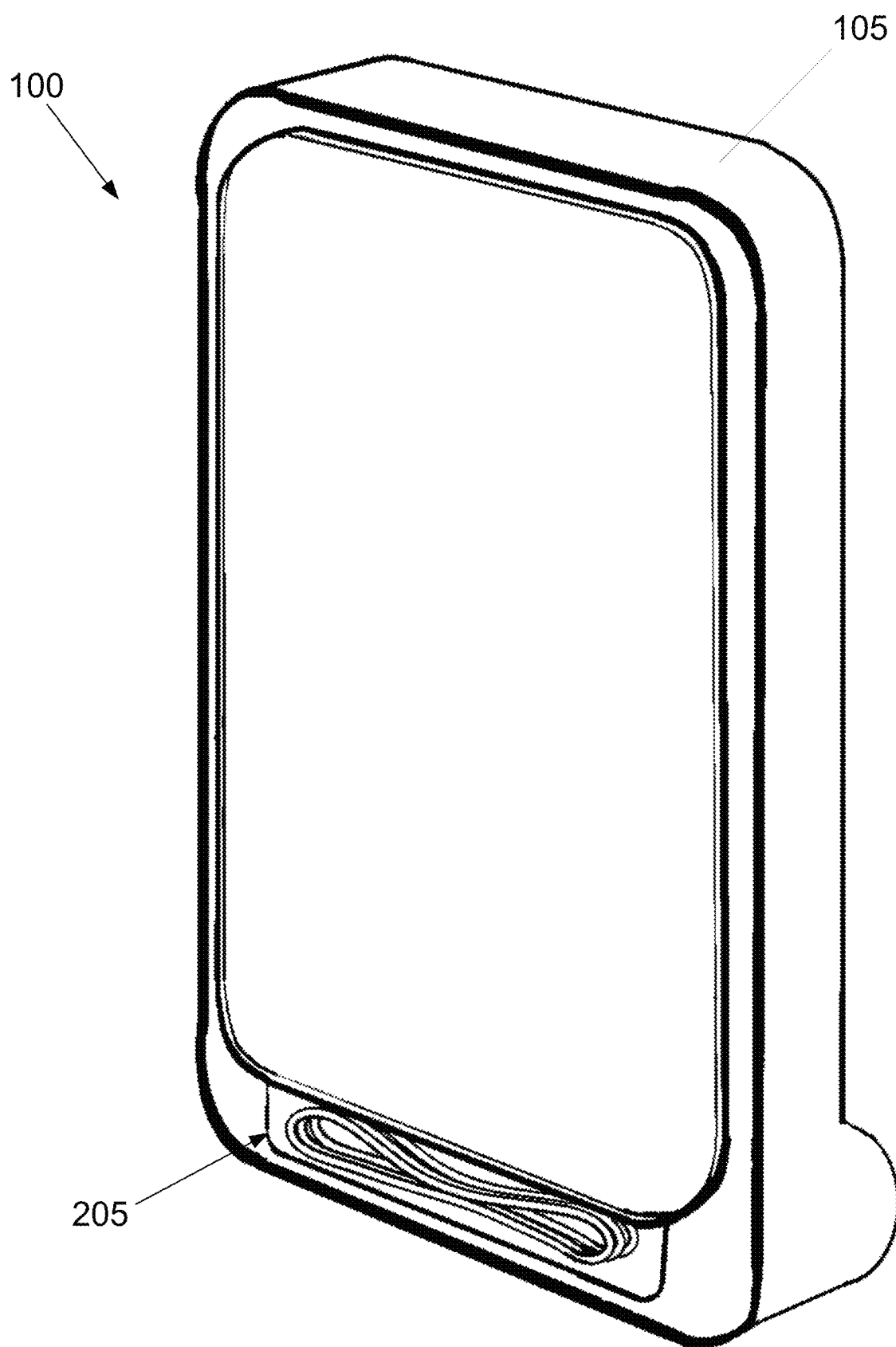
FIG. 2 is a perspective view of the compact AED with one distal electrode without a rear cover.

The distal electrode (115) does not require a typical electrical connector like other AEDs (such as a plug), makes contact to the connecting electrode (130) on the device body (105) of the AED, and only requires a single wire or cord. The wire (120) preferably stores in a carve-out (205) toward the rear of the device body immediately to the front of where the rear cover (465) would go when added to device body shown in FIG. 2.

Most commonly, the gel used for AED electrodes is typically an adhesive gel, such as hydrogel. Typically, no other adhesive coating is needed with this type of gel. Optionally, the proximate pad (405) may be coated with one or more adhesives on each side of the proximate pad (405) for attachment to the proximate electrode (110) and for attachment to the person (601) once the distal electrode (115) is unpacked. While the adhesive may be used at different locations within the AED and may be the same adhesive in composition, each adhesive at a different location is given a distinct name to accommodate the potential for different adhesives being used and to avoid confusion. The adhesive that sticks to a person's skin is referred to as a skin adhesive (905). The adhesive used to stick the proximate pad (405) to the proximate electrode (110), to stick the distal pad (410) to the distal electrode (115), and to stick the insulating cover (132) and wire (120) to the connecting electrode (130) is referred to as an electrode adhesive (910). Finally, the adhesive used to seal the device body (105) from air infiltration is referred to as the adhesive (320), which is preferably a silicone adhesive.

The distal electrode (115) is electrically connected from the device body (105) by a wire (120). The wire (120) must be of sufficient gauge and otherwise configured to deliver the electrical charge (605) to the distal electrode (115) from the device body (105). The distal electrode (115) is configured to be replaceable and further configured to be operable by the circuit board (415) in the device body (105). No other circuit board positioned outside the device body, for example, one in or on the distal electrode is needed. Preferably, the distal electrode (115) is configured to be exclusively operable by the circuit board (415) in the device body (105).

Preferably, the circuit board (415) in device body (105) of the compact automated external defibrillator (100) is configured to deliver a reversal of the electrical polarity of the electrical charge (605) during the time the AED is delivering a charge to the person (601). This is termed a biphasic charge or shock. With any biphasic shock, the direction of current flow is reversed during the electrical defibrillation cycle. In the preferred embodiment of the compact automated external defibrillator (100), such reversal is implemented at least one time while delivering the electrical charge (605).

Preferably, the circuit board (415) is configured to be an indivisible unit within the device body (105). This means that the circuit board (415) is not separable into two or more circuit board components. While there may be more than one printed circuit board (PCB) within the device body (105), none such PCB may be broken off from another PCB and preferably, none is located in the distal electrode (115).

The compact automated external defibrillator (100) preferably employs the proximate pad (405) on the device body (105) so that the proximate pad (405) may be peeled off the device body (105). While an electrical plug provides a relatively easy means for disconnecting any electrical component, the preferred connection for the proximate electrode (110) to the circuitry within the device body (105) is one involving electrical contact with the circuit board. A clip, a fastener, hydrogel and/or an adhesive may be employed to secure this contact.

The compact automated external defibrillator (100) is preferably configured with the wire (120) composed of strands (125) of smaller diameter wires. The strands (125) are attached to the device body (105) after splaying the strands (125) on a terminal or connecting electrode (130) on the device body (105). The strands (125) may be embedded in a hardened, electrically conducting gel (431), preferably hydrogel, to make adhesion to the connecting electrode (130) easier for replacement. This arrangement is shown in FIG. 4 where the splayed wires are embedded in a hardened, electrically conducting gel (431), such as hydrogel, which can then be adhered to the connecting electrode (130). For that arrangement, there is preferably an insulating cover (432) over the gel and wires to insulate them. Because the distal electrode (115) and the proximate electrode (110) have separated electrical connections a biphasic shock is made possible. The wire (120) that connects the distal electrode (115) to the device body (105) is preferably splayed to flatten or minimize the height or profile of the connections.

In another alternative embodiment, the strands (125) that are embedded in a hardened, electrically conducting gel (431) are adhered to carbon-loaded vinyl, tin, or silver with electrode adhesive (910) which may be the same material as the hardened, electrically conducting gel (431). The carbon-loaded vinyl, tin or silver is covered with the insulating cover (432).

In another alternative embodiment, the strands (125) that are embedded in a hardened, electrically conducting gel (431) are folded between a carbon-loaded vinyl, tin, or silver, which are electrically conductive materials. The hardened, electrically conductive gel (431) and the strands (125) are adhered to the carbon-loaded vinyl, tin, or silver with an electrode adhesive (910), which may be the same material as the hardened, electrically conducting gel (431). The carbon-loaded vinyl, tin or silver is covered with the insulating cover (432).

Similarly, the wire connection at the other end of the wire (120) on the distal electrode (115) may use splayed strands. The wire (120) is preferably attached to the distal electrode (115) after splaying its strands (125) on the distal electrode (115).

The distal electrode (115) preferably comprises a metal conductor (preferably tin or silver) with a distal pad (410) on one side next to the liner (335) adhered to the metal conductor and a foam pad (460) covering the other side of the metal conductor next to a packing cover (455). Preferably, the foam pad (460) distal electrode (115), and distal pad (410) is a unit. Once used, this unit is disconnected and discarded, along with the wire and a new unit is installed with a new wire. In another embodiment, the distal pad (410) is configured to be peeled off and removed from the distal electrode (115) when a replacement distal pad is needed. In addition, the distal electrode (115) is configured to be disconnected from the connecting electrode (130) at the device body (105). For example, this may be accomplished by peeling off the wire (120) and hydrogel from the connecting electrode (130), by removing the wire (120) from the connecting electrode (130), by unplugging from the device body (105), or by any other means. In an alternative embodiment, the proximate electrode (110) can also be disconnected from the device body when an electrical plug is not present, such as when it may need to be replaced for maintenance, in the event is it combined with the proximate pad (405), or any other reason. In yet another embodiment, the connecting electrode can also be disconnected from the device body when an electrical plug is not present, such as when it may need to be replaced for maintenance, in the event is it combined with the insulating cover (432), or any other reason.

The device body (105) is configured to store the proximate electrode (110) separated from the distal electrode (115) by a liner (335). The liner (335) is preferably a thin plastic sheet that can be easily pulled off both electrodes to free them from their storage position. Thus, the device body (105) is preferably configured to store the proximate electrode and the distal electrode (115) within the device body (105) separated by the liner (335).

The liner (335) is preferably configured to define a hole (425) through which an electrical connection is made between the pads on the proximate electrode (110) and the distal electrode (115) enabling activation of a check on the operability of a discharge circuit. This electrical connection facilitates periodic testing of the AED pads, for example the hydrogel, by the compact automated external defibrillator (100) when activated to do a simple connectivity test. Doing this would validate that the user has correctly stored the pads and that the electrical path is valid (i.e., the hydrogel has not dried out).

The discharge circuit is an electrical path from the device body (105) that houses the proximate electrode (110), through the hole (425) to the distal electrode (115), and back through the wire (120). In an alternative embodiment, the discharge circuit is an electrical path from the device body (105) through the wire (120) to the distal electrode (115), through the hole (425), to the proximate electrode (110).

When in use, the circuit board (415) is configured to deliver the electrical charge (605) through the connecting electrode (130), through the wire (120) through the distal electrode (115) where the electrical charge (605) passes through the person (601) and ends at the proximate electrode (110). When a biphasic charge is employed, the circuit board (415) is also configured to deliver the electrical charge (605) through the proximate electrode (110), through the person (601), through the distal electrode (115), through the wire (120), and end at the connecting electrode (130). In other embodiments of a biphasic shock, the first electrical path may begin with the proximate electrode and then switch to the distal electrode.

Figure 7:
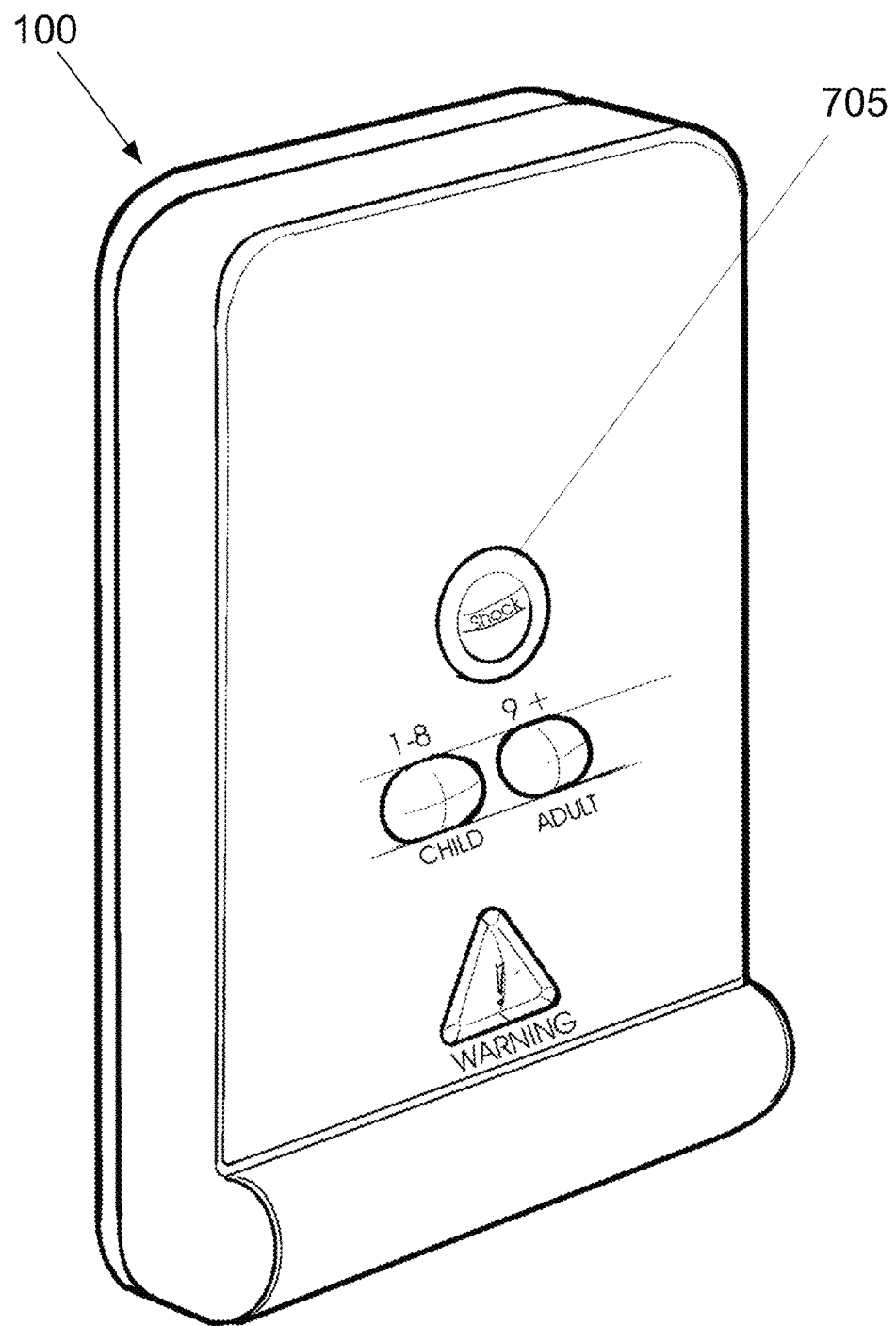
FIG. 7 is a perspective view of the front of the compact AED with one distal electrode.

As an example, FIG. 7 shows an activation button (705) along with other controls on the front face of the compact automated external defibrillator (100). In this embodiment, the activation button (705) enables use of the AED to send the electrical charge (605) 15 through the person (601). Other embodiments include automatic activation of the AED, for example when an arrhythmia is detected.

Figure 3:
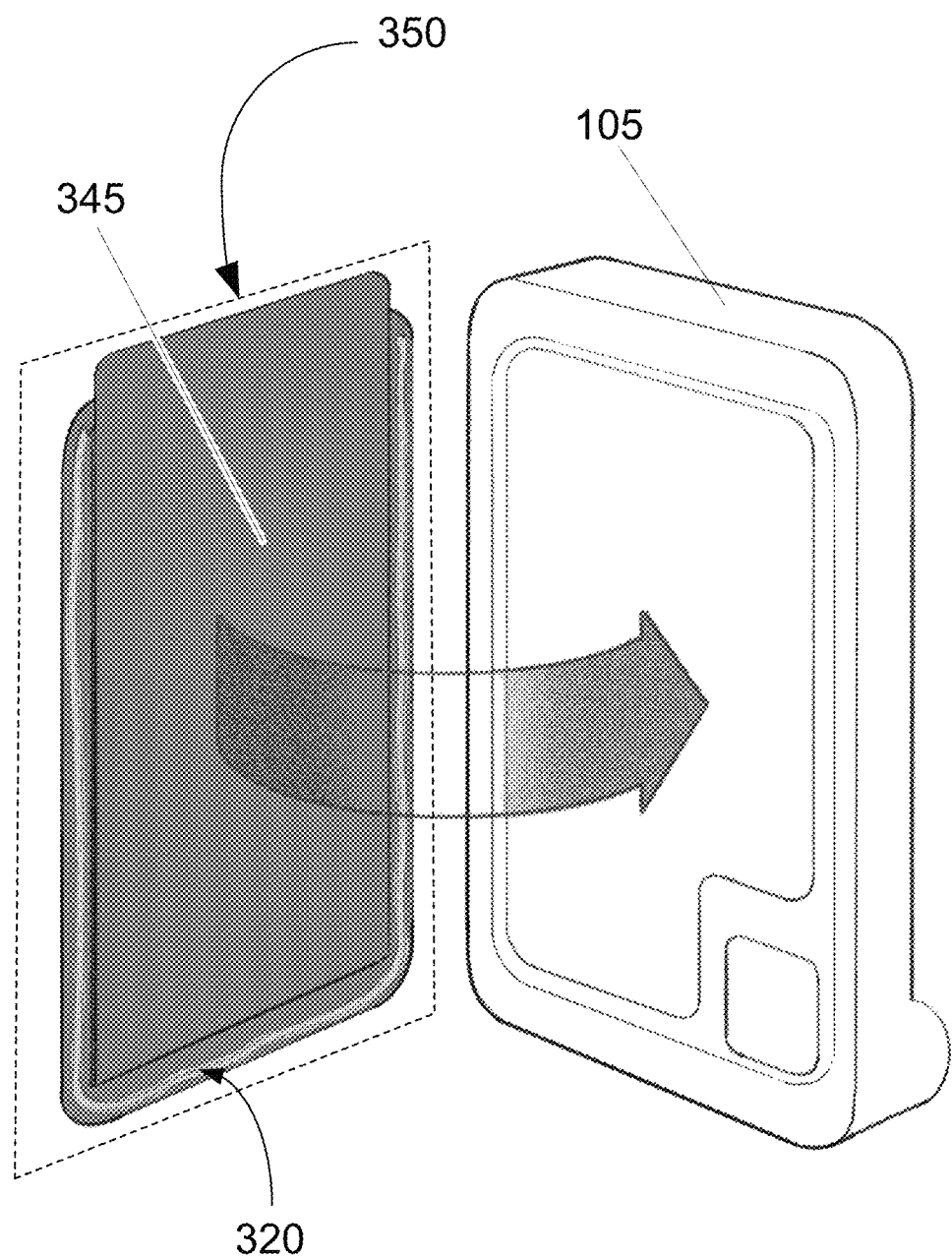
FIG. 3 is a perspective view of the device body and packaging envelope.

A packaging envelope (350) is shown in FIG. 3 within the rectangular dashed box. A pull-tab (345) may be used to unseal the packaging envelope (350). The packaging envelope (350) is configured to seal the proximate pad (405) and distal pad (410) to help keep them or prevent them from drying out when in storage, and the pull-tab (345) is configured to easily open the packaging envelope (350) during a rescue in order to reveal the proximate pad (405) and align it to the proximate electrode (110).

A metalized surface (420) on the device body (105) may be applied to help seal the device body (105) from air entering and leaving the device body (105). Among other benefits, the metalized surface (420) prevents the pads from drying out. Thus, the metalized surface (420) is configured to seal the device body (105) when the components of the AED are in storage.

Figure 8:
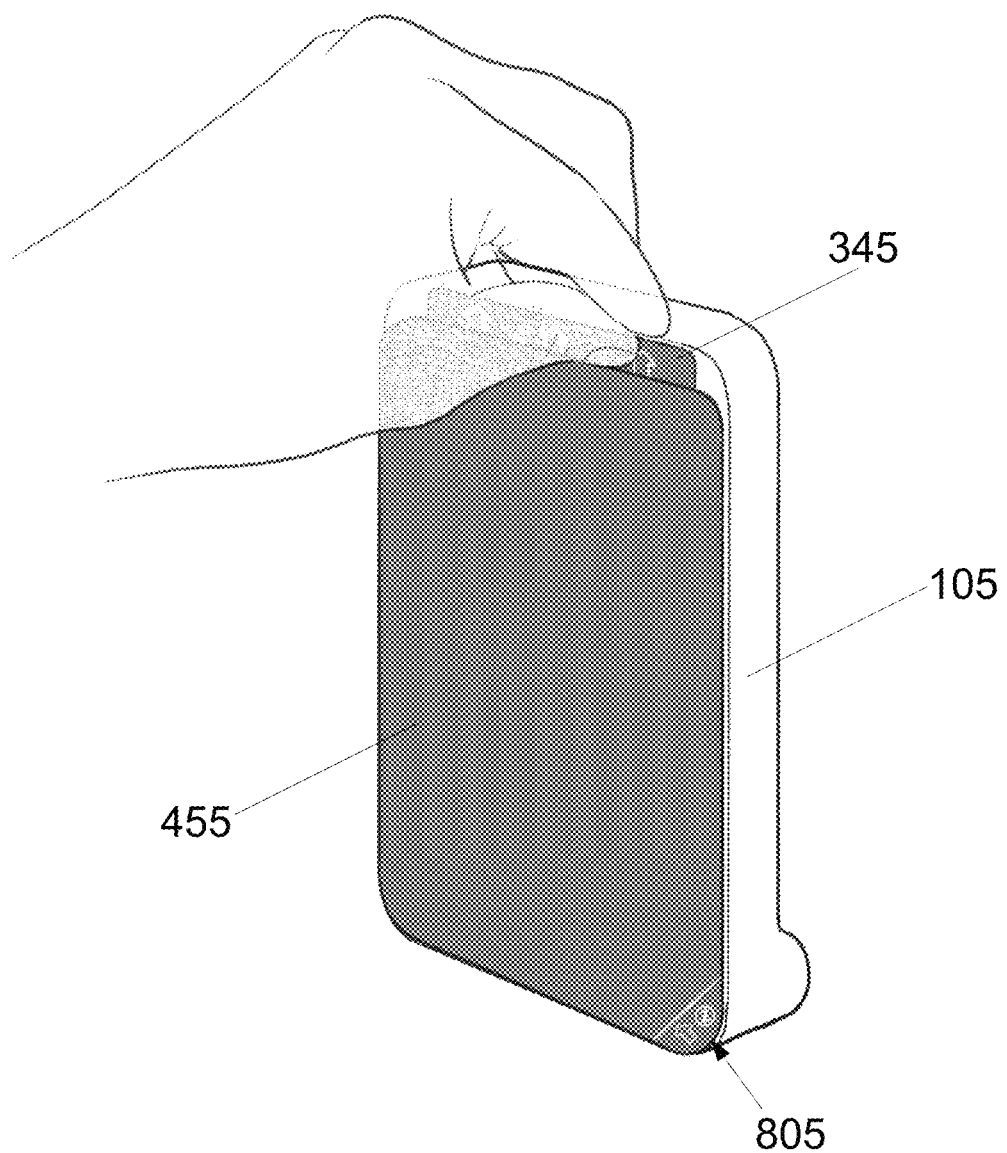
FIG. 8 is rear view of the device body with a packing cover over a packaging envelope with a pull-tab.
Figure 9:
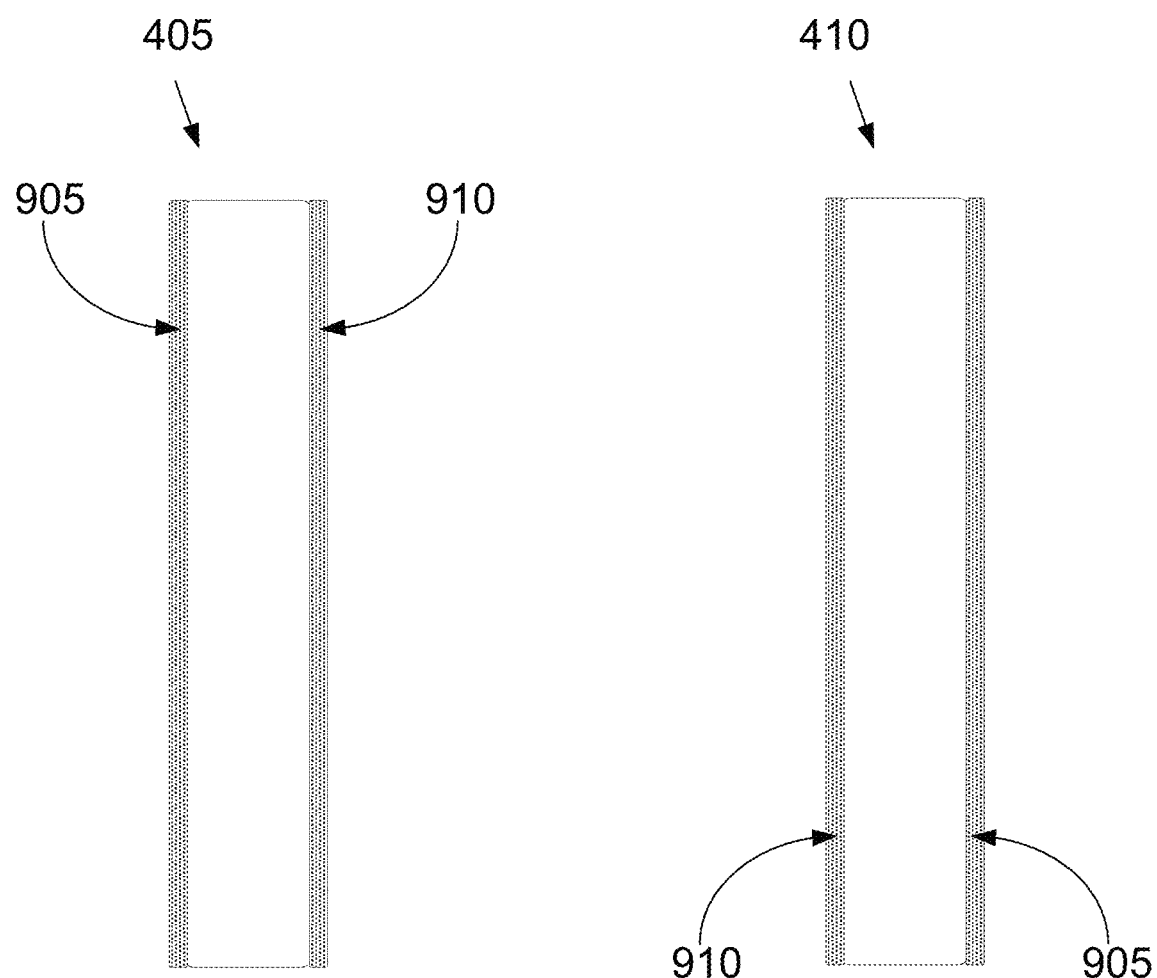
FIG. 9 is a side view of the proximate pad and the distal pad showing the skin adhesive and the electrode adhesive.

As shown in FIG. 4, a rear cover (465) is a rigid closure for the device body (105). The rear cover (465), for example, could be a hard plastic. An adhesive (320), such as silicone, may be used on the periphery of the packaging envelope (350) to engage with the device body (105). Additionally, a packing cover (455) may be included to help seal up the device body (105) when the components are stored therein. The packing cover (455), like the rear cover (465), is preferably made of a light weight material, such as plastic, foam, or that is metalized material. For example, a metalized coating or seal would be peeled away at the corner or edge of the device. A peelable corner tab (805) is shown in FIG. 8 for the lower right-hand corner of the packing cover (455).

In an alternative embodiment, the packing cover (455) may serve to replace the foam pad (460), revealing the distal electrode (115) and distal pad (410) underneath of it once removed.

Figure 10:
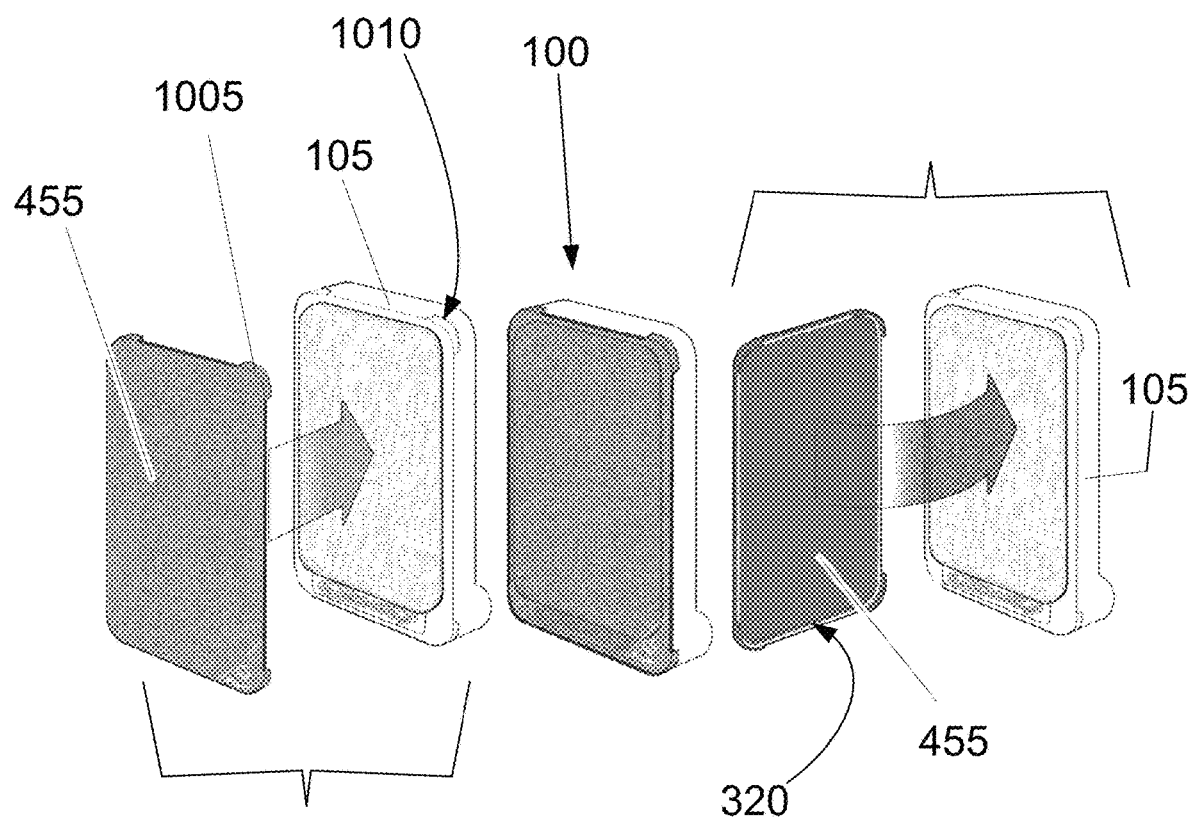
FIG. 10 is a perspective view of an alternative embodiment where the rear cover and packing cover are combined, to comprise a plastic that has an adhesive around the periphery to seal to the device body.

In an alternative embodiment shown in FIG. 10, the rear cover (465) may be combined with the packing cover (455), designated packing cover (455) in FIG. 10. The packing cover (455) is composed of plastic and is sealed to the device body (105) with adhesive (320) around the periphery of the packing cover (455). The adhesive (320) is preferably silicone adhesive. In another embodiment, the packing cover (455) may be configured with a corner clip (1005), preferably 4 corner clips at each corner of the packing cover (455). Such clips may also be present on the rear cover (465) and the rear cover (465) itself may also be sealed to the device body with adhesive (320). Preferably, each corner clip (1005) mates with a notch (1010) on the device body (105), which ensures a tight fit, and a seal by the adhesive (320). The plastic of the packing cover (455) may seal against a metalized surface on the device body (105) to help prevent air infiltration.

In another embodiment, the rear cover (465) may be configured with a mechanism, such as a notch or clip, to mate with a mechanism on the device body (105), such as a notch or clip, to ensure proper orientation of the connecting electrode (130).

In another alternative embodiment, the packing cover (455) may serve to replace the rear cover (465), revealing the distal assembly, namely the foam pad (460), distal electrode (115) and distal pad (410), underneath of it once removed. Adhesive sealant around the inside of the packing cover (455) connects to the device body (105) and prevents air infiltration to the pads.

In sum, important component parts of the compact automated external defibrillator (100) include: the foam pad (460), the distal electrode (115), and the distal pad (410), which are an assembly, and which adhere to the person in cardiac distress; the electrodes, including the distal electrode (115) and the proximate electrode (110), which are conductive metals, preferably tin or silver, which form the conductive portion that connect to the person in cardiac distress and also the distal electrode (115) is the component that connects to the wire (120) that then connects to the device body (105); the distal pad (410) and the proximate pad (405), which are preferably made of hydrogel and which include an electrically conductive gel that adheres each electrode to the patient and that creates a lower resistance electrical path to the patient; the proximate electrode (110) and the distal electrode (115), which are electrically conductive elements that are connected to AED's internal circuitry.

The above-described embodiments including the drawings are examples of the compact automated external defibrillator (100) and merely provide illustrations of the compact automated external defibrillator (100). Other embodiments will be obvious to those skilled in the art. Thus, the scope of the compact automated external defibrillator (100) is determined by the appended claims and their legal equivalents rather than by the examples given.

INDUSTRIAL APPLICABILITY

The compact automated external defibrillator (100) has application to the medical industry.

What is claimed is:

1. A compact automated external defibrillator configured to deliver an electrical charge to a person in cardiac distress, the compact automated external defibrillator configured for reuse on another person, the compact automated external defibrillator comprising:
   a device body;
   a circuit board configured as an indivisible unit within the device body;
   a proximate pad configured to be electrically connected to a proximate electrode and once so connected, the proximate pad together with the device body configured for attachment to the person; and the proximate pad further configured to be removable from the proximate electrode;
   a distal electrode connected from the device body by a wire, the wire configured to deliver the electrical charge to the distal electrode from the device body, the distal electrode comprising a distal pad, the distal pad configured to be replaceable and the distal electrode further configured to be operable by no other circuit board positioned outside the device body;
   the device body mates with a rear cover in a configuration that prevents air infiltration to the proximate pad and the distal pad prior to deployment of the compact automated external defibrillator; and
   the device body further configured to store the proximate electrode and the distal electrode, the device body further comprising a liner, wherein the liner separates the proximate electrode from the distal electrode when the proximate electrode and the distal electrode are stored within the device body.

2. The compact automated external defibrillator of claim 1, wherein the circuit board is configured for a reversal of electrical polarity of the electrical charge, such reversal implemented at least one time while delivering the electrical charge.

3. The compact automated external defibrillator of claim 1, wherein the proximate pad on the device body is configured to be peeled off the device body.

4. The compact automated external defibrillator of claim 1, wherein the proximate electrode in the device body is configured to be disconnected from the device body when an electrical plug is not present.

5. The compact automated external defibrillator of claim 1, wherein the wire comprises strands and is attached to the device body after splaying the strands on a terminal on the device body.

6. The compact automated external defibrillator of claim 1, wherein the wire comprises strands and is attached to the distal electrode after splaying the strands on the distal electrode.

7. The compact automated external defibrillator of claim 1, wherein the distal electrode comprises a second pad, the distal electrode configured to be removable by separation from the device body.

8. The compact automated external defibrillator of claim 1, wherein the liner is configured to define a hole through which an electrical connection is made between the proximate electrode and the distal electrode enabling activation of a check on operability of a discharge circuit, the discharge circuit comprising an electrical path from the device body, through the hole to the distal electrode, and through the wire configured to deliver the electrical charge to the distal electrode from the device body.

9. The compact automated external defibrillator of claim 1, further comprising a packaging envelope, the packaging envelope configured to seal the proximate pad and the distal pad to prevent them from drying out when in storage.

10. The compact automated external defibrillator of claim 9 further comprising a pull-tab on the packaging envelope, the pull-tab configured to open the packaging envelope during a rescue in order to connect the proximate pad to the proximate electrode.

11. The compact automated external defibrillator of claim 1, further comprising a metalized surface on the device body, the metalized surface configured to seal the device body.

* * * * *